US007393952B2

(12) United States Patent
Maryanoff et al.

(10) Patent No.: US 7,393,952 B2
(45) Date of Patent: Jul. 1, 2008

(54) SOLVENT FREE AMORPHOUS RAPAMYCIN

(75) Inventors: Cynthia A. Maryanoff, New Hope, PA (US); Karel Six, Hulste (BE); Roger Vandecruys, Westerlo (BE)

(73) Assignee: Cordis Corporation, Miami Lakes, FL (US)

(*) Notice: Subject to any disclaimer, the term of this patent is extended or adjusted under 35 U.S.C. 154(b) by 189 days.

(21) Appl. No.: 11/210,393

(22) Filed: Aug. 24, 2005

(65) Prior Publication Data

US 2006/0128739 A1     Jun. 15, 2006

Related U.S. Application Data

(60) Provisional application No. 60/605,324, filed on Aug. 27, 2004.

(51) Int. Cl.
*C07D 498/18*     (2006.01)
(52) U.S. Cl. ..................................................... 540/456
(58) Field of Classification Search ................. 540/456
See application file for complete search history.

(56) References Cited

U.S. PATENT DOCUMENTS 3,929,992 A     12/1975     Seghal et al. ................. 424/122

FOREIGN PATENT DOCUMENTS

| WO | 94/09010 A1 | 4/1994 |
|---|---|---|
| WO | 97/03654 A2 | 2/1997 |
| WO | 01/87893 A1 | 11/2001 |
| WO | 02/057228 A1 | 7/2002 |
| WO | 2004/028582 A1 | 4/2004 |
| WO | 2005/011688 A1 | 2/2005 |
| WO | 2005/023254 A1 | 3/2005 |

OTHER PUBLICATIONS

Berk, B. C. et al., "Heparins and Glucocorticoids Inhibit Restenosis," J. Am. Coll. Cardiol., 1991, 17, 111B-117B.
Campbell, G. R. and Campbell, J. H., "Phenotypic Modulation of Smooth Muscle Cells in Primary Culture," In: *Vascular Smooth Muscle in Culture*, vol. 1, Ch. 4, Boca Raton, FL: CRC, 1987, pp. 39-55.
Campbell, G. R., et al., "Smooth muscle phenotypic changes in arterial wall homeostasis: implications for the pathogenesis of atherosclerosis," Exp. Mol. Pathol., Apr. 1985, 42(2), 139-162.
Chang, M. W. et al., "Adenovirus-mediated Over-expression of the Cyclin/Cyclin-dependent," J. Clin. Invest., 1995, 96, 2260-2268.
Clowes, A. W. et al., "Kinetics of cellular proliferation after arterial injury. IV. Heparin inhibits rat smooth muscle mitogenesis and migration," Circ. Res., 1986, 58(6), 839-845.
Clowes, A. W. et al., "Kinetics of cellular proliferation after arterial injury. II. Inhibition of smooth muscle growth by heparin," Lab. Invest., 1985, 52(6), 611-616.
Clowes, A. W. et al., "Significance of quiescent smooth muscle migration in the injured rat carotid artery," Circ Res. 1985, 56(1), 139-145.
Clowes, A. W., "Suppression by heparin of smooth muscle cell proliferation in injured arteries," Nature, 1977, 265(5595), 625-626.
Colburn, M. D. et al., "Dose responsive suppression of myointimal hyperplasia by dexamethasone," J. Vasc. Surg., 1992, 15, 510-518.
Currier, J. W. et al., "Colchicine Inhibits Restenosis After Iliac Angioplasty in the Atherosclerotic Rabbit," Circ., 1989, 80(4), 11-66 (Abstract No. 0263).
Edelman, E. R. et al., "Pathobiologic responses to stenting," Am J. Cardiol. 1998, 81(7A), 4E-6E.
Farb, A. et al., "Vascular smooth muscle cell cytotoxicity and sustained inhibition of neointimal formation by fibroblast growth factor 2-saporin fusion protein," Circ. Res., 1997, 80, 542-550.
Ferns, G. A. A. et al., "Inhibition of Neointimal Smooth Muscle Accumulation After Angioplasty by an Antibody to PDGF," Science, 1991, 253, 1129-1132.
Fischman, D. L. et al., "A Randomized Comparison of Coronary-Stent Placement and Balloon Angioplasty in the Treatment of Coronary Artery Disease," N. Eng. J. Med., Aug. 25, 1994, 331(8), 496-501.
Franklin, S. M. et al., "Pharmacologic prevention of restenosis after coronary angioplasty: review of the randomized clinical trials," Coron Artery Dis. Mar. 1993, 4(3), 232-242.
Fukuyama, J. et al., "Tranilast suppresses the vascular intimal hyperplasia after balloon injury in rabbits fed on a high-cholesterol diet," Eur. J. Pharmacol., 1996, 318, 327-332.
Guyton, J. R. et al., "Inhibition of rat arterial smooth muscle cell proliferation by heparin. In vivo studies with anticoagulant and nonanticoagulant heparin," Circ. Res., 1980, 46, 625-634.

(Continued)

*Primary Examiner*—Bruck Kifle
(74) *Attorney, Agent, or Firm*—Carl J. Evens (57) ABSTRACT

An improved process for coating implantable medical devices utilizes a number of techniques for improving the stability of therapeutic agents contained within the coating. The stability of the therapeutic agents may be improved by creating substantially solvent-free, amorphous forms of the therapeutic agents.

1 Claim, 8 Drawing Sheets

OTHER PUBLICATIONS

Hancock, B. C. et al., "The Relationship Between the Glass Transition Temperature and the Water Content of Amorphous Pharmaceutical Solids," *Pharmaceutical Research*, 1994, 11(4), 471-477, XP008031768.

Hanson, S. R. et al., "Interruption of acute platelet-dependent thrombosis by the synthetic antithrombin D-phenylalanyl-L-prolyl-L-arginyl chloromethyl ketone," Proc. Natl. Acad. Sci. USA, 1988, 85, 3184-3188.

Jonasson, J. et al., "Cyclosporin A inhibits smooth muscle proliferation in the vascular response to injury," Proc. Natl., Acad. Sci., 1988, 85, 2303-2306.

Lang, R. J. et al., "Effects of 2,3-butanedione monoxime on whole-cell Ca2+ channel currents in single cells of the guinea-pig taenia caeci," J Physiol. Feb. 1991, 433, 1-24.

Lang, R. J. et al., "Effects of okadaic acid and ATP gamma S on cell length and Ca(2+)-channel currents recorded in single smooth muscle cells of the guinea-pig taenia caeci.,", Br. J. Pharmacol., Oct. 1991, 104(2), 331-336.

Liu, M. W. et al., "Trapidil in Preventing Restenosis After Balloon Angioplasty in the Atherosclerotic Rabbit," Circ., 1990, 81, 1089-1093.

Lundergan, C. F. et al., "Peptide Inhibition of Myointirnal Proliferation by Angiopeptin, a Somatostatin Analogue," Am. J. Cardiol., 1991, 17(Suppl. B), 132B-136B.

Majesky, M. W. et al., "Heparin regulates smooth muscle S phase entry in the injured rat carotid artery," Circ. Res., 1987, 61, 296-300.

Mak, K-H. et al., "Clinical trials to prevent restenosis after percutaneous coronary revascularization," Ann N Y Acad Sci., Apr. 15, 1997, 811, 255-84; discussion 284-8. Review.

Marx, S. O. et al., "Rapamycin-FKBP Inhibits Cell Cycle Regulators of Proliferation in Vascular Smooth Muscle Cells," Circ. Res., 1995, 76, 412-417.

Nemecek, G. M. et al., "Terbinafine Inhibits the Mitogenic Response to Platelet-Derived Growth Factor in Vitro and Neoinimal Proliferation in Vivo," J. Pharmacol. Exp. Thera., 1989, 248, 1167-1174.

Okada, T. et al., "Localized Release of Perivascular Heparin Inhibits Intimal Proliferation after Endothelial Injury without Systemic Anticoagulation," Neurosurgery, 1989, 25, 92-98.

Popma, J. J. et al , "Atherectomy of right coronary ostial stenoses: initial and long-term results, technical features and histologic findings," Am J Cardiol., Feb. 15, 1991; 67(5), 431-433.

Popma, J. J. et al., "Adjuncts to thrombolysis for myocardial reperfusion," Ann Intern Med., Jul. 1, 1991, 115(1), 34-44.

Popma, J. J. et al., "Clinical trials of restenosis after coronary angioplasty," Circulation, Sep. 1991, 84(3), 1426-1436.

Popma, J. J. et al., "Clinical, angiographic and procedural correlates of quantitative coronary dimensions after directional coronary atherectomy," J Am Coll Cardiol., Nov. 1, 1991, 18(5), 1183-1189.

Powell, J. S. et al., "Inhibitors of Angiotensin-Converting Enzyme Prevent Myointimal Proliferation After Vascular Injury," Science, 1989, 245, 186-188.

Serruys, P. W. et al., "A comparison of balloon-expandable-stent implantation with balloon angioplasty in patients with coronary artery disease," N Engl J Med, Aug. 25, 1994; 331(8), 489-495.

Serruys, P. W. et al., "Evaluation of ketanserin in the prevention of restenosis after percutaneous transluminal coronary angioplasty. A multicenter randomized double-blind placebo-controlled trial," Circulation, Oct. 1993; 88(4 Pt 1), 1588-1601.

Serruys, P. W. et al., "Heparin-coated Palmaz-Schatz stents in human coronary arteries. Early outcome of the Benestent-II Pilot Study," Circulation, Feb. 1, 1996; 93(3), 412-422.

Serruys, P. W. et al., "Randomized trials of coronary stenting," J Interv Cardiol, Aug. 1994; 7(4), 331.

Serruys, P. W. et al., "Restenosis revisited: insights provided by quantitative coronary angiography," Am Heart J, Nov. 1993; 126(5), 1243-1267.

Serruys, P. W. et al., "The bailout stent. Is a friend in need always a friend indeed?" Circulation, Nov. 1993; 88(5 Pt 1), 2455-2457.

Simons, M. et al., "Antisense c-*myb* oligonucleotides inhibit intimal arterial smooth muscle cell accumulation in vivo," Nature, 1992, 359, 67-70.

Snow, A. D. et al., "Heparin modulates the composition of the extracellular matrix domain surrounding arterial smooth muscle cells," Am. J. Pathol., 1990, 137, 313-330.

Sollot, S. J. et al., "Taxol Inhibits Neointimal Smooth Muscle Cell Accumulation after Angioplasty in the Rat," J. Clin. Invest., 1995, 95, 1869-1876.

Tanaka, H. et al., "Sustained activation of vascular cells and leukocytes in the rabbit aorta after balloon injury," Circulation, Oct. 1993; 88(4 Pt 1), 1788-1803.

Tardif, et al., "Probucol and multivitamins in the prevention of restenosis after coronary angioplasty. Multivitamins and Probucol Study Group," N Engl J Med. Aug. 7, 1997; 337(6), 365-372.

Teirstein, P. S. et al., "Catheter-based radiotherapy to inhibit restenosis after coronary stenting," N Engl J Med., Jun. 12, 1997; 336(24), 1697-1703.

Weinberger, J. et al., "Intracoronary irradiation: dose response for the prevention of restenosis in swine," Int. J. Rad. Onc. Biol. Phys., 1996, 36, 767-775.

Yokoi, H. et al., "Effectiveness of an antioxidant in preventing restenosis after percutaneous transluminal coronary angioplasty: the Probucol Angioplasty Restenosis Trial," J Am Coll Cardiol., Oct. 1997; 30(4), 855-862.

International Search Report PCT/US2005/030606 dated Feb. 6, 2006.

SOLVENT FREE AMORPHOUS RAPAMYCIN

CROSS REFERENCE TO RELATED APPLICATION

This application claims the benefit of U.S. Provisional Patent Application Ser. No. 60/605,324 filed Aug. 27, 2004.

BACKGROUND OF THE INVENTION

1. Field of the Invention

The present invention relates to methods for coating stents with therapeutic agents and more particularly to developing and utilizing stable, amorphous therapeutic agents for coating stents as well as for other applications.

2. Discussion of the Related Art

Many individuals suffer from circulatory disease caused by a progressive blockage of the blood vessels that profuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans, which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll. Cardiol. 17: 111B-117B, 1991), ionizing radiation (Weinberger, J. et al., Int. J. Rad. Onc. Biol. Phys. 36: 767-775, 1996), fusion toxins (Farb, A. et al., Circ. Res. 80: 542-550, 1997) antisense oligionucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is through diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

While the selection of an appropriate therapeutic agent and an appropriate coating in which to incorporate the therapeutic agent is important, maintaining the stability of the agent is also important. Accordingly, there exists a need for developing a process for coating the implantable medical device that incorporates steps to stabilize the therapeutic agent. In addition, there exists a need for creating more stable formulations of the therapeutic agent or agents.

SUMMARY OF THE INVENTION

The processes of the present invention provide a means for overcoming the difficulties associated with the coating of implantable medical devices with therapeutic agents and with the creation of substantially solvent-free amorphous forms of therapeutic agents. Substantially solvent-free amorphous forms of therapeutic agents are typically more stable and typically have an increased solubility that allows for better uptake of the agent.

In accordance with a first aspect, the present invention is directed to a method of preparing amorphous rapamycin. The method comprises dissolving rapamycin in 2-propanol to form a solution forming an amorphous rapamycin precipitate by adding water to the solution and drying the amorphous rapamycin precipitate for a predetermined period of time.

In accordance with another aspect, the present invention is directed to amorphous rapamycin produced by the following process. The process comprises dissolving rapamycin in 2-propanol to form a solution, forming an amorphous rapamycin precipitate by adding water to the solution, and drying the amorphous rapamycin precipitate for a predetermined period of time.

In accordance with another aspect, the present invention is directed to amorphous rapamycin having a glass transition temperature in the range from about 92 degrees C. to about 95 degrees C.

In accordance with another aspect, the present invention is directed to a method of preparing amorphous rapamycin. The method comprises dissolving rapamycin in 2-propanol to form a solution and forming an amorphous rapamycin precipitate by adding water to the solution.

In accordance with another aspect, the present invention is directed to a amorphous rapamycin produced by the following process. The process comprises dissolving rapamycin in 2-propanol to form a solution and forming an amorphous rapamycin precipitate by adding water to the solution.

The process of the present invention incorporates a number of steps to increase the stability of the therapeutic agent, including protecting the therapeutic agent from autoxidation by increasing the glass transition temperature of the agent, reducing the presence of and/or exposure of various materials which contain free radicals and autoxidation initiators, and reducing the presence of and/or exposure of the various materials to oxygen. The glass transition temperature of the therapeutic agent may be raised via a separate process in order to create a substantially solvent-free amorphous form of the therapeutic agent. As stated above, amorphous forms of therapeutic agents typically have increased solubility which in turn means better uptake upon administration in any form.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention is directed to a process for coating stents or other implantable medical devices with one or more therapeutic agents, such as a rapamycin. One exemplary process is set forth in the flow chart of FIG. 1. The first part of the process comprises the primer application. In the exemplary embodiment, the first step in the process is surface preparation and treatment, step 102. This step involves utilizing a cleaning solution to remove endotoxins from the stents to be coated. The cleaning solution may comprise any number of cleaning solutions, for example, a high pH solution such as a potassium hydroxide solution containing silicates. The next step is also a surface preparation and treatment step, step 104. In this step a silane solution is utilized to prepare the surfaces of the stents for the deposition of a primer layer. The next step is the application of the primer itself, step 106. In this exemplary embodiment, parylene is applied to the stents utilizing a vapor deposition process. Once the parylene is applied, the stents are packaged and weighed, step 108. Once the stents are weighed, they are placed in containers or vials. The vials may be formed from any number of suitable materials. In the exemplary embodiment, the vials are formed from polypropylene.

Figure 1:
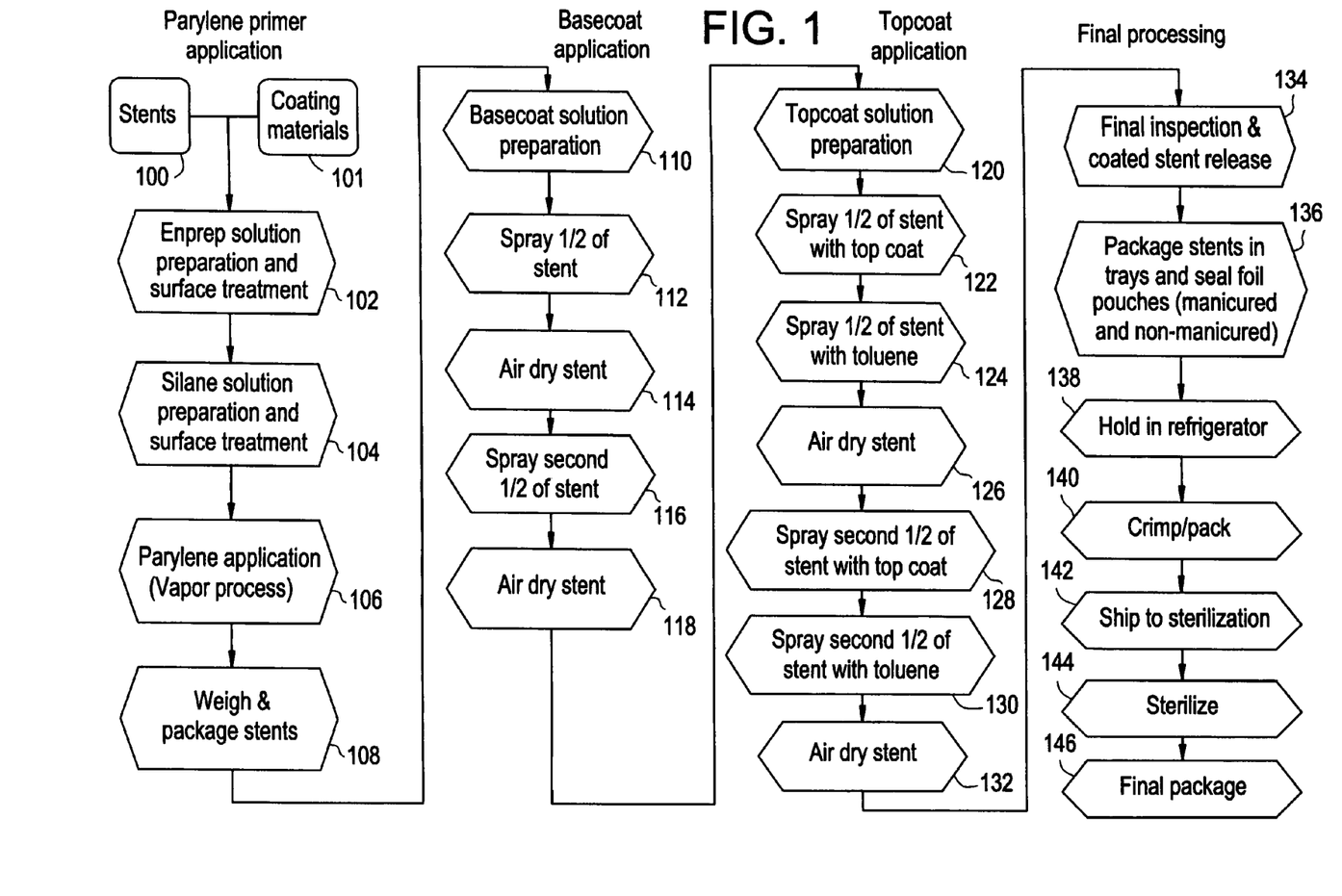
FIG. 1 is a flow chart of a first exemplary embodiment of a process for coating stents in accordance with the present invention.

The second part of the process comprises the basecoat application. The first step in the second part of the process is the preparation of the basecoat solution, step 110. The basecoat solution may comprise any suitable biocompatible polymers and therapeutic agents. The therapeutic agents and polymers should preferably be compatible. In the exemplary embodiment, the basecoat solution comprises polyethylene co-vinylacetate, polybutylmethacrylate and a rapamycin, such as sirolimus. The solution is prepared in a standard reactor. The solution is decanted into smaller containers for the next step. The next step is the coating of the stents, step 112. In this step, the stents are coated with the basecoat solution. The stents may be coated in any suitable manner. In the exemplary embodiment, the stents are coated utilizing a spray coating technique. Nitrogen is utilized as the carrier gas for the basecoat solution. In step 112, one half of the stent is coated and then air dried in step 114. The half coated stents are dried at a relative humidity of about thirty to about fifty-five percent for about thirty minutes. The air temperature is held at about room temperature. The air in the drying chamber is continuously recirculated. Upon completion of the drying step 114, the second half of the stent is coated, step 116 and then dried again in step 118. Steps 116 and 118 are identical to steps 112 and 114.

The third part of the process comprises the topcoat application. The first step in the third part of the process is the preparation of the topcoat solution, step 120. The preparation of the topcoat comprises preparing a solution of polybutylmethacrylate. Once the topcoat application is prepared and decanted into a spraying container, one-half of the stent is coated, step 122. The next step of the process is another coating step, step 124. In this coating step, the half of the stents that have been a topcoat application are sprayed with toluene. The spraying of toluene has a polishing effect on the topcoat and also facilitates elution control of the therapeutic agent from the polymeric topcoat application. Once step 124 is complete, the stents are air dried, step 126, under the same conditions as in steps 114 and 118. Steps 128, 130 and 132 are the same as steps 122, 124 and 126 but for the second half of the stents.

The fourth and final part of the exemplary process comprises the final processing. The first step in the fourth part of the process is final inspection and coated stent release, step 134. Each of the stents is inspected for defects. Various inspection techniques such as microscopy may be utilized to determine if the stents meet various rigorous standards. The next step in the process is packaging, step 136. The stents are put into trays and sealed in pouches. In this exemplary embodiment, the trays are PETG trays. Once the stents are packaged, they are refrigerated, step 138. The stents are maintained at a temperature from about five degrees centigrade to about eight degrees centigrade. Wider ranges may be utilized. The next step in the process is the crimping and packaging of each of the stents, step 140. In this step, the stents are positioned on the delivery device and crimped to the desired size. Once positioned on the delivery devices, the whole system is packaged and shipped to a location for sterilization, steps 142 and 144. The systems are sterilized utilizing ethylene oxide, but other suitable sterilization processes may be utilized. The final step of the process is final packaging, step 146.

Figure 2:
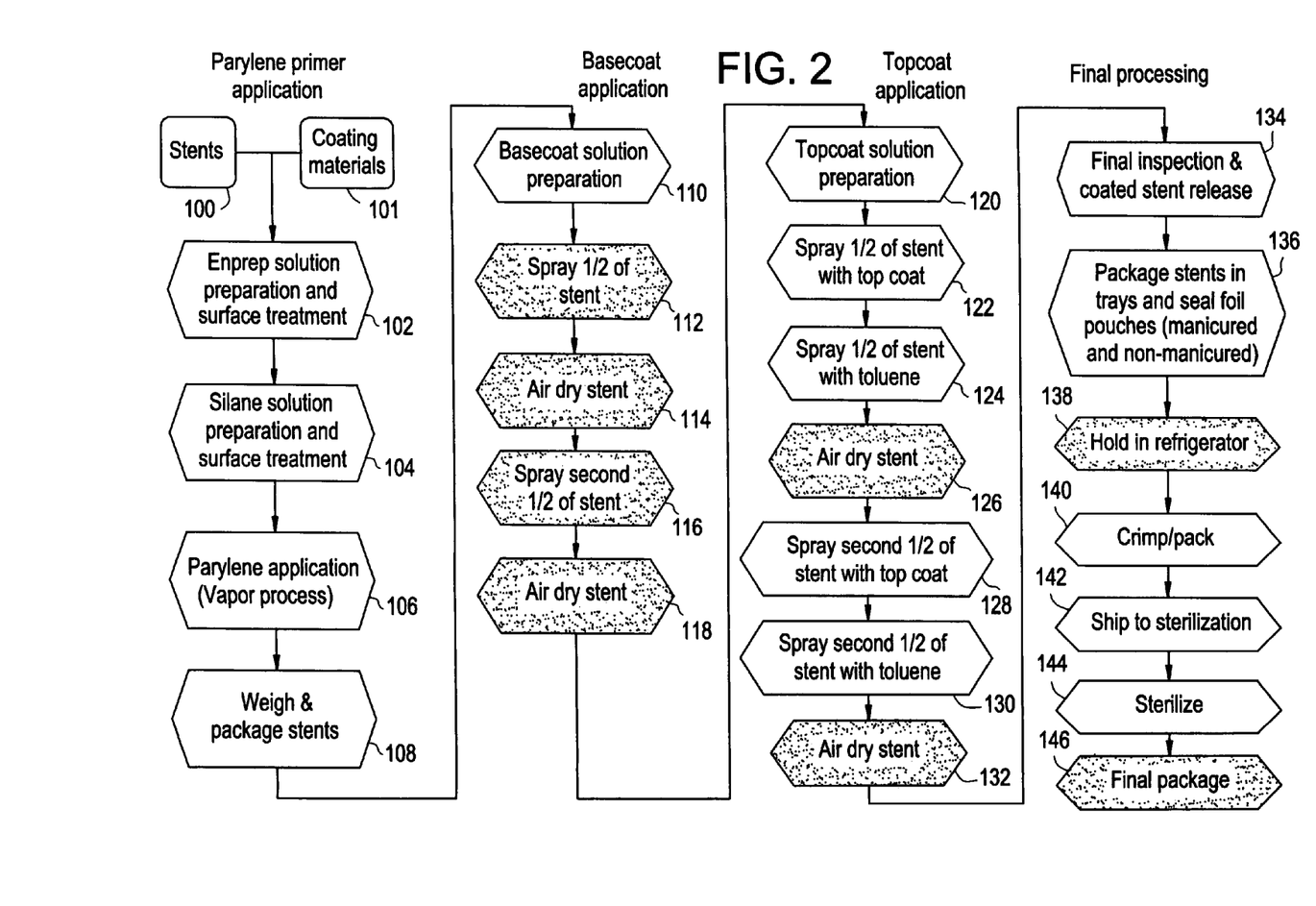
FIG. 2 is a flow chart of a second exemplary embodiment of a process for coating stents in accordance with the present invention.

A number of process modifications may be utilized to address autoxidation. Autoxidation occurs when there is a fuel, in this case the therapeutic agent, an ignition of the fuel, in this case radicals, and finally, there is oxygen or oxygen containing compounds. The first process modification includes protecting the active pharmaceutic ingredient or therapeutic agent, sirolimus in this embodiment, from autoxidation. One way in which to protect the active pharmaceutical ingredient is to raise its glass transition temperature, Tg. A higher glass transition temperature leads to a more stable therapeutic agent at room temperature. Amorphous substances act like sponges and will pick up other compounds such as solvents. Sirolimus is an amorphous therapeutic agent. Accordingly, in order to make an amorphous therapeutic agent more stable, one has to raise its glass transition temperature and since solvents lower the glass transition temperature, the minimization of exposure to residual solvents is required. Ways in which to reduce or minimize exposure to residual solvents include keeping extraneous solvents away from the coating, for example, cleaning agents and solvent bottles, and storing stents in an environment that is substantially solvent free, for example, away from freshly coated stents and/or from solutions. Preferably, the therapeutic agents or stents coated with therapeutic agents are stored in stability chambers. In addition, a higher glass transition temperature may be achieved by increasing the removal of residual solvents post coating. This may be accomplished by allowing more time for residual solvent removal post coating, by applying vacuum conditions and heat to enhance residual solvent removal and by allowing short-term moisture exchange (presence of humidity) to enhance residual solvent removal. The long-term exposure to relative humidity is preferably controlled because humidity may act as a plasticizer. Vacuum packaging and packaging under inert gas of the finished goods addresses this concern. Also, the three domain coating morphology, i.e., three different zones of polymer and therapeutic agent offers only some protection of the therapeutic agent from oxygen. Accordingly, the spraying conditions may be modified to control or affect the coating morphology, for example, low humidity and spray head distance. The steps of the process that may be modified to accomplish these improvements include steps 112, 114, 116, 118, 126, 132, 138 and 146 as illustrated in FIG. 2.

Figure 3:
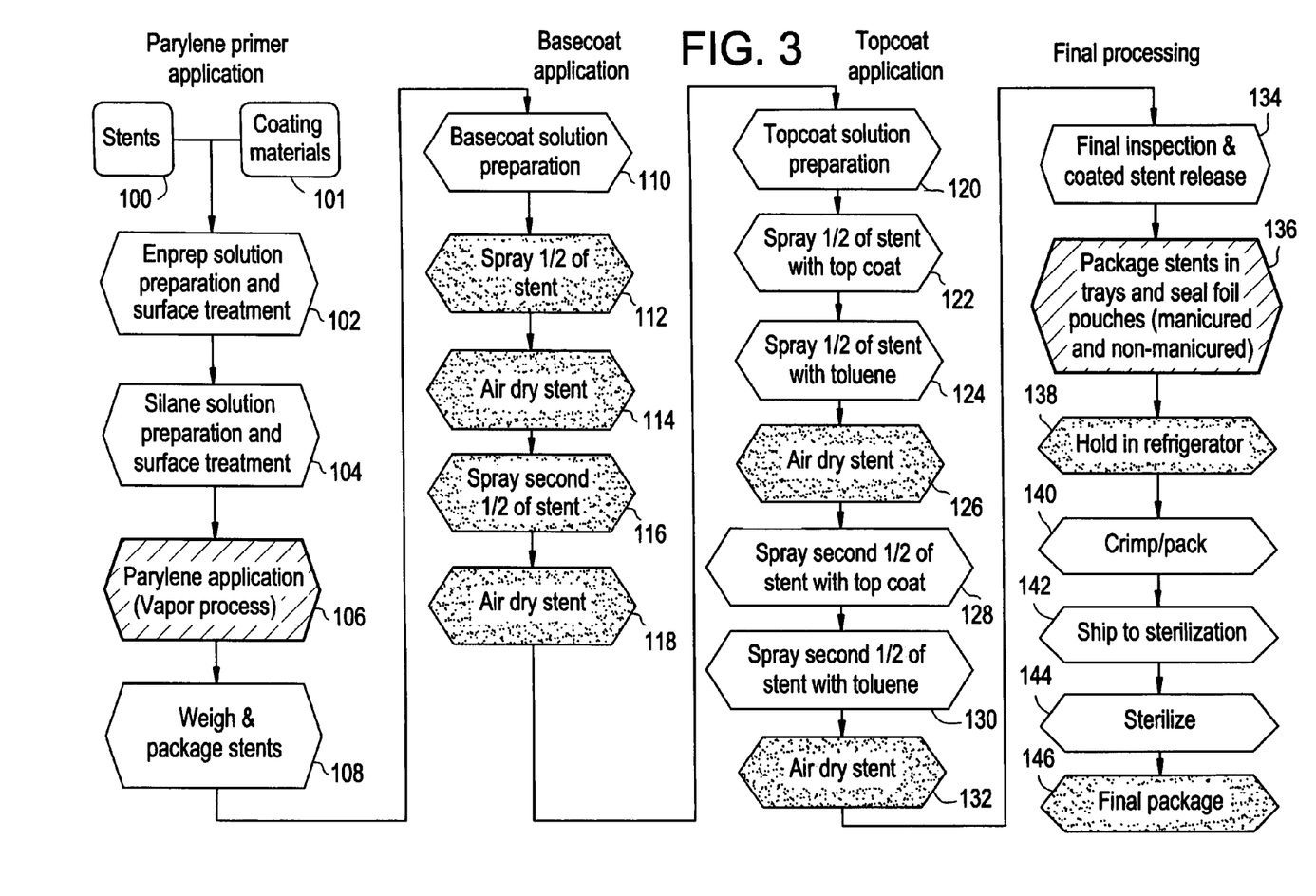
FIG. 3 is a flow chart of a third exemplary embodiment of a process for coating stents in accordance with the present invention.

Another process modification comprises reducing the presence of and/or exposure to free radicals and, autoxidation initiators. This may be accomplished by utilizing materials with minimal free radicals, for example, polypropylene vials may be utilized rather than PETG trays, and utilizing tools to assist in the crimping and packaging stage that are fabricated from inert materials. This may also be accomplished by parylene annealing to reduce parylene radicals. The steps of the process that may be modified to accomplish these improvements include steps 104 and 136 as illustrated in FIG. 3.

Figure 4:
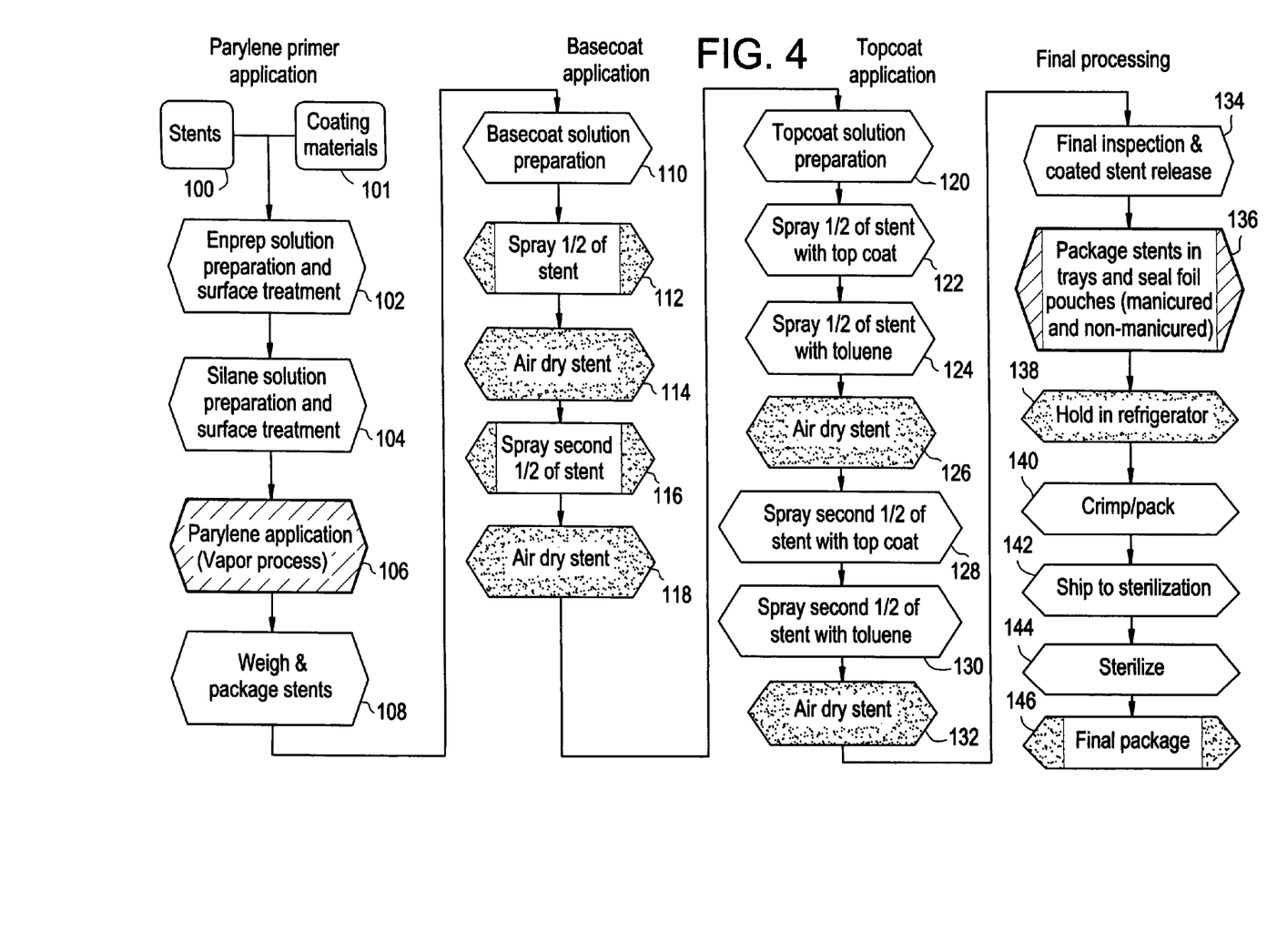
FIG. 4 is a flow chart of a fourth exemplary embodiment of a process for coating stents in accordance with the present invention.

Yet another process modification comprises reducing the presence of and/or exposure to oxygen. This may be accomplished by having improved controls of raw materials, improved coating solution mixing and handling, and improved coatings. Improved control of raw materials includes solvents such as THF with low hydroperoxides and an active pharmaceutic ingredient with minimal handling. Improved coating solution mixing and handling includes inert gas blanketing to reduce dissolved oxygen and the minimization of all decanting steps. Improved coating includes spraying in a nitrogen rich environment, vacuum oven, purging with inert gas after annealing and vacuum packaging, and/or packaging under inert gas of works in progress and finished goods. The steps of the process that may be modified to accomplish these improvements include steps 101, 110, 112, 116, 120, 136 and 146 as illustrated in FIG. 4.

It is important to note that although stents are discussed in detail herein, the local delivery of drug/drug combinations may be utilized to treat a wide variety of conditions utilizing any number of medical devices, or to enhance the function and/or life of the device. For example, intraocular lenses, placed to restore vision after cataract surgery, are often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The process modifications described above may be utilized to improve the coatings on stents as well as other implantable medical devices. However, other process may also be utilized to develop more stable forms of therapeutic agents for use with implantable medical devices as well as other forms of delivery.

A therapeutic agent, for example, sirolimus (rapamycin), may be prepared or processed in a manner such that it is in a stable form that may be administered in any number of ways. For example, the sirolimus may be administered orally, parenterally, intravascularly, intranasally, intrabronchially, transdermally, rectally or via a stent coated with sirolimus. In the exemplary embodiment described herein, crystalline sirolimus may be processed into a substantially solvent free amorphous solid form with a glass transition temperature of about 93 degrees C. The glass transition is a property of amorphous materials. When an amorphous material is heated to a temperature above its glass transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Accordingly, the higher the glass transition temperature for a given amorphous material, the more stable or less reactive the material is under room temperature and pressure (RTP) conditions. In addition, amorphous forms of therapeutic agents typically have increased solubility, which in turn means better uptake of the therapeutic agents by the patient.

The preparation of substantially solvent free amorphous sirolimus with a glass transition temperature, $T_g$, of about 93 degrees C. comprises the following steps. First, a given amount of crystalline sirolimus is dissolved in an appropriate solvent. It is important to note that any number of solvents or combinations of solvents may be utilized. In the exemplary embodiment, 250 mg of crystalline sirolimus is placed in a 100 ml beaker to which 4 ml of 2-propanol is added. The mixture may be slightly heated and mixed to facilitate the dissolution of the sirolimus. Next, the solution is stirred while an agent is added to the solution to precipitate the sirolimus from solution. In the exemplary embodiment, the solution is continuously stirred with a magnetic stirrer while 50 ml of water is added in order to precipitate the sirolimus. It is important to note that any number of agents may be utilized to precipitate the sirolimus from solution. The product of this step is an amorphous precipitate. The concentration of sirolimus in solution determines the length of time required to precipitate the sirolimus from solution. Next, the amorphous precipitate is filtered and washed. In the exemplary embodiment, the amorphous precipitate is passed through a 0.45 μm pore filter under vacuum to remove the supernatant. The filtered amorphous precipitate is then washed with 100 ml of water to remove impurities. In the next and final step, the precipitate is dried. In the exemplary embodiment, the precipitate is dried for a period ranging from about 18 hours to about 36 hours at a temperature of about 30 degrees C. and under a vacuum of about 150 mBar. The result is a substantially solvent free amorphous solid form of sirolimus with a glass transition temperature of about 93 degrees C. that may be utilized in a polymer as described above or in any other suitable form as described subsequently.

Figure 5:
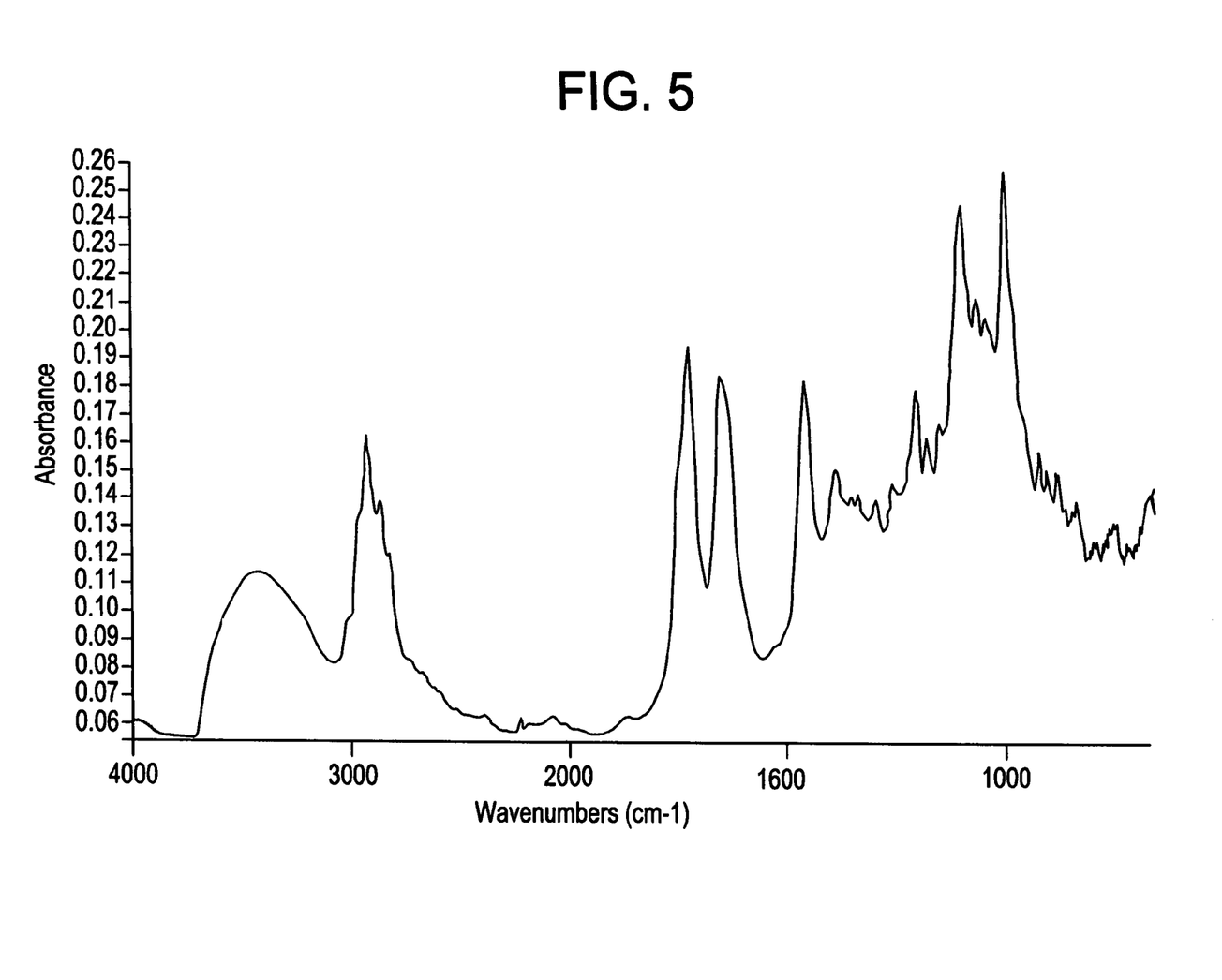
FIG. 5 is an ATR-infrared spectrum of amorphous solutions prepared in accordance with the present invention.

A number of tests or evaluations may be performed in order that the substantially solvent free amorphous sirolimus may be characterized. In one test, the amorphous sirolimus is analyzed utilizing a micro attenuated total reflectance (ATR) infrared spectrometer. Essentially, the purpose of this test is to determine if the amorphous sirolimus prepared by the above-described process is degraded in any significant way. Table 1, given below, contains a summary of the test parameters. FIG. 5 is the ATR-infrared spectrum of amorphous sirolimus prepared utilizing the above-described process. As illustrated in FIG. 5, the infrared spectrum of the prepared sirolimus reflects the vibrational modes of the molecular structure of sirolimus as an amorphous product. In other words, the sirolimus was not degraded during the process.

TABLE 1

| micro Attenuated Total Reflectance Infrared Spectroscopy | |
| --- | --- |
| Number of scans: | 32 |
| Resolution: | 1 cm-1 |
| Wavelength range: | 4000 to 400 cm-1 |
| Apparatus: | Nicolet Magna 560 FTIR spectrophotometer |
| Baseline correction: | yes |
| Detector: | DTGS with KBr windows |
| Beam splitter: | Ge on KBr |
| Micro ATR accessory: | Harrick Split Pea with Si crystal |

Figure 6:
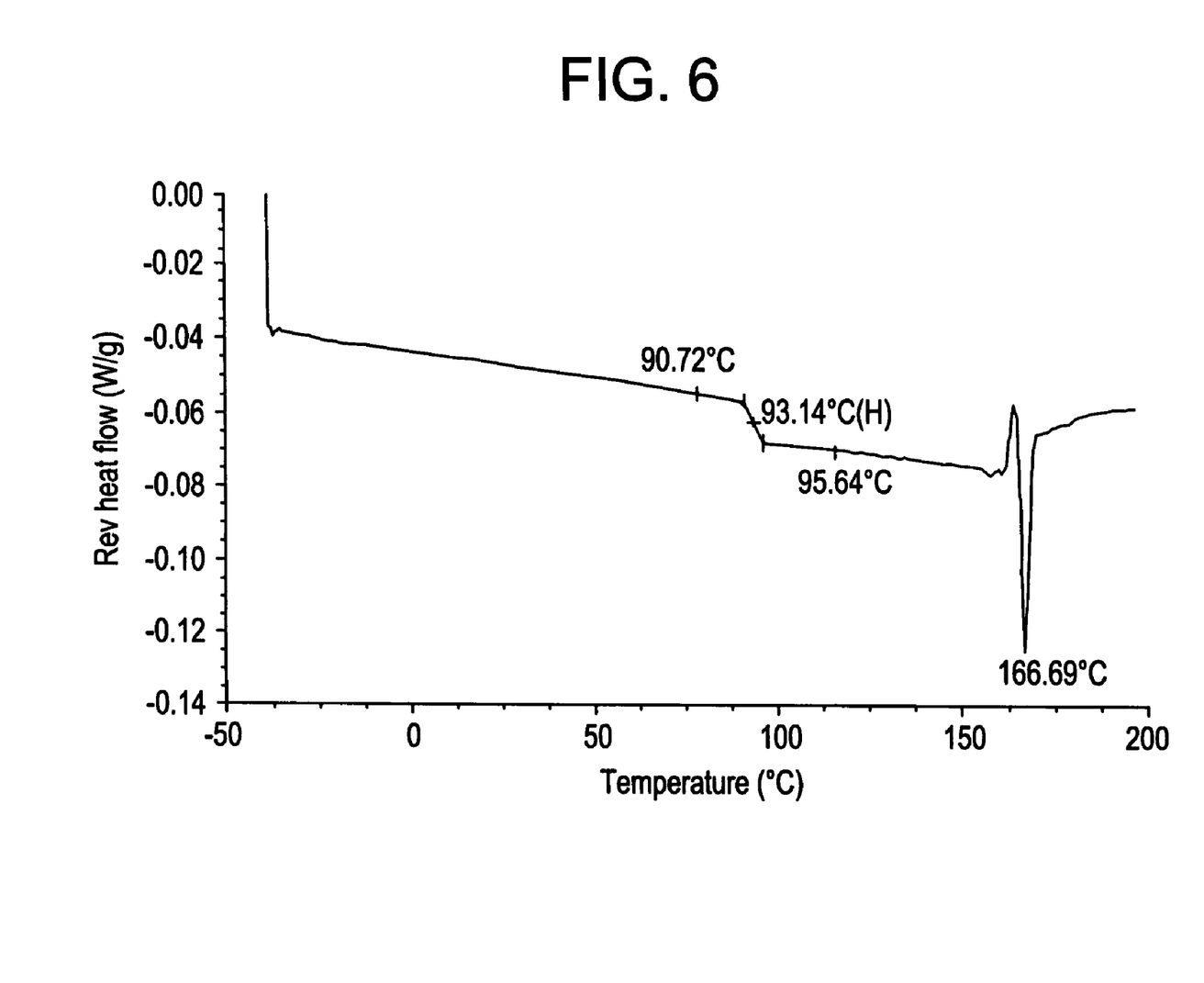
FIG. 6 is a differential scanning calorimetry curve of amorphous solutions prepared in accordance with the present invention.

In another test, the amorphous sirolimus is analyzed utilizing differential scanning calorimetry (DSC). Essentially, the purpose of this test is to determine the glass transition temperature of the amorphous sirolimus. In this test, approximately 3 mg of amorphous sirolimus is transferred into a standard aluminum TA-Instrument sample pan and covered. The DSC curve is recorded on a TA-Instruments Q1000 MTDSC equipped with a RCS cooling unit. Table 2, given below, contains a summary of the test parameters. FIG. 6 illustrates a differential scanning calorimetry (DSC) curve of amorphous sirolimus. The differential scanning calorimetry curve for this sample shows the glass transition temperature of the amorphous sirolimus to be about 93 degrees C. Based on a number of scans, the glass transition temperatures may be in the range from about 92 degrees C. to about 95 degrees C.

TABLE 2

Differential Scanning Calorimetry

| | First Heating |
|---|---|
| Initial temperature | −40° C. |
| Heating rate | 2° C./min |
| Final temperature | 200° C. |
| Nitrogen flow | 30 ml/min |
| Amplitude | 0.318° C. |
| Period | 60 s |

Figure 7:
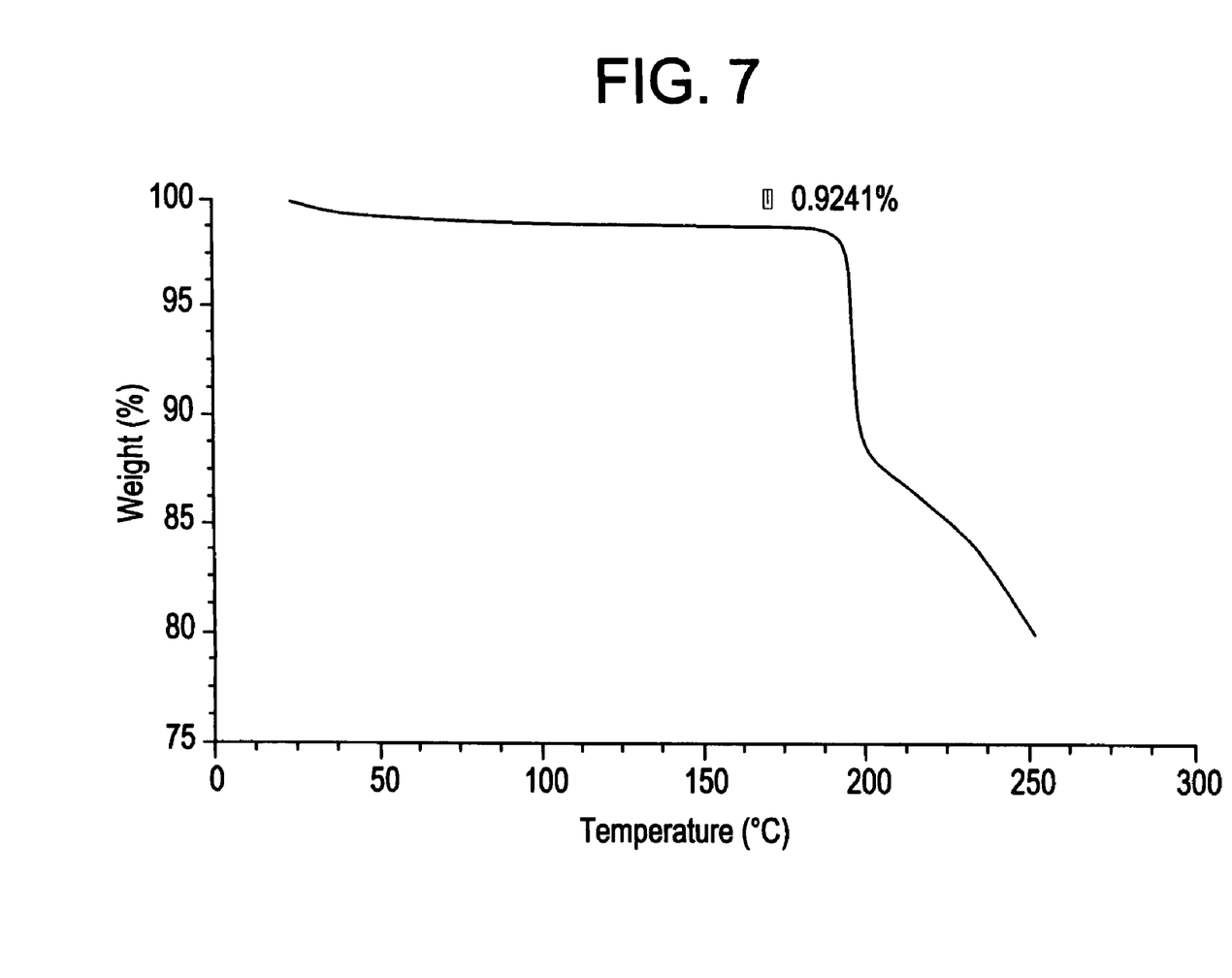
FIG. 7 is a thermogravity curve of amorphous solutions prepared in accordance with the present invention

In another test, the amorphous sirolimus is analyzed utilizing a thermogravitometer. Essentially, the purpose of this test is to determine weight loss in the amorphous sirolimus. In this test, the amorphous sirolimus is transferred into an aluminum sample pan and placed in a thermogavimeter (TG). The TG curve is recorded utilizing a TA Instruments Hi-Res TGA 2950 thermogavimeter. Table 3, given below, contains a summary of the test parameters. FIG. 7 illustrates a thermogravity curve of amorphous sirolimus. As is illustrated, a loss of sample weight occurs from about 25 degrees C. to about 160 degrees C. This small weight loss may be due to the evaporation of absorbed water and 2-propanol. A second weight loss is observed when the compound decomposes.

TABLE 3

Thermogravimetry

| Initial temperature: | room temperature |
|---|---|
| Heating rate: | 20° C./min |
| Resolution factor: | 4 |
| Final condition: | 300° C. or <80 [(w/w)%] |

In yet another test, the amorphous sirolimus is analyzed utilizing a gas chromatograph. Essentially, the purpose of this test is to determine the chemical composition of the sample, in particular, the residual solvent content. In this test, 15 mg of amorphous sirolimus is placed in a vial and dissolved in 2 ml of DMSO. The vial is closed and analyzed utilizing the parameters listed in Table 4, given below. The results of the test indicate that the amorphous sirolimus contains 77 ppm of 2-propanol.

TABLE 4

Gas Chromatography

| GC system | | Parameters |
|---|---|---|
| Column | | 50 m fused silica column with an ID of 0.32 mm, coated with a chemically bonded polydimethylsiloxane (CP-SIL 5 CB) of 5 µm film thickness. comment: |
| Carrier gas | | Gas: nitrogen 5.5 Gas: Hydrogen Pi: 100 kPa Mode: constant pressure comment: |
| Injector | | Type: Splitter dynamic splitting: 0–30 ml/min split insert: fritted temperature: 230° C. comment: |
| Detector | | Type: FID Temperature: 270° C. gases: hydrogen: 23–31 ml/min air: 285–315 ml/min make up: 20–25 ml/min sensitivity: range 12 (1 × 10³ pA/V) comment: |
| Headspace autosampler | Bath temperature: | 80° C. |
| | Loop temperature: | 230° C. |
| | Loop volume: | 5 ml |
| | Equilibration time: | 55 min |
| | Pressure time on vial: | 2 min |
| | Pressure hold time: | 0.2 min |
| | Loop fill time: | 1 min |
| | Loop equilibration time: | 0.2 min |
| | Injection time: | 0.5 min. |
| | Transfer line temperature: | 230° C. |
| | Vial pressure: | ~50 kPa |
| | Transfer line pressure: | ~120 kPa |

TABLE 4-continued

Gas Chromatography

GC system Parameters

Figure 8:
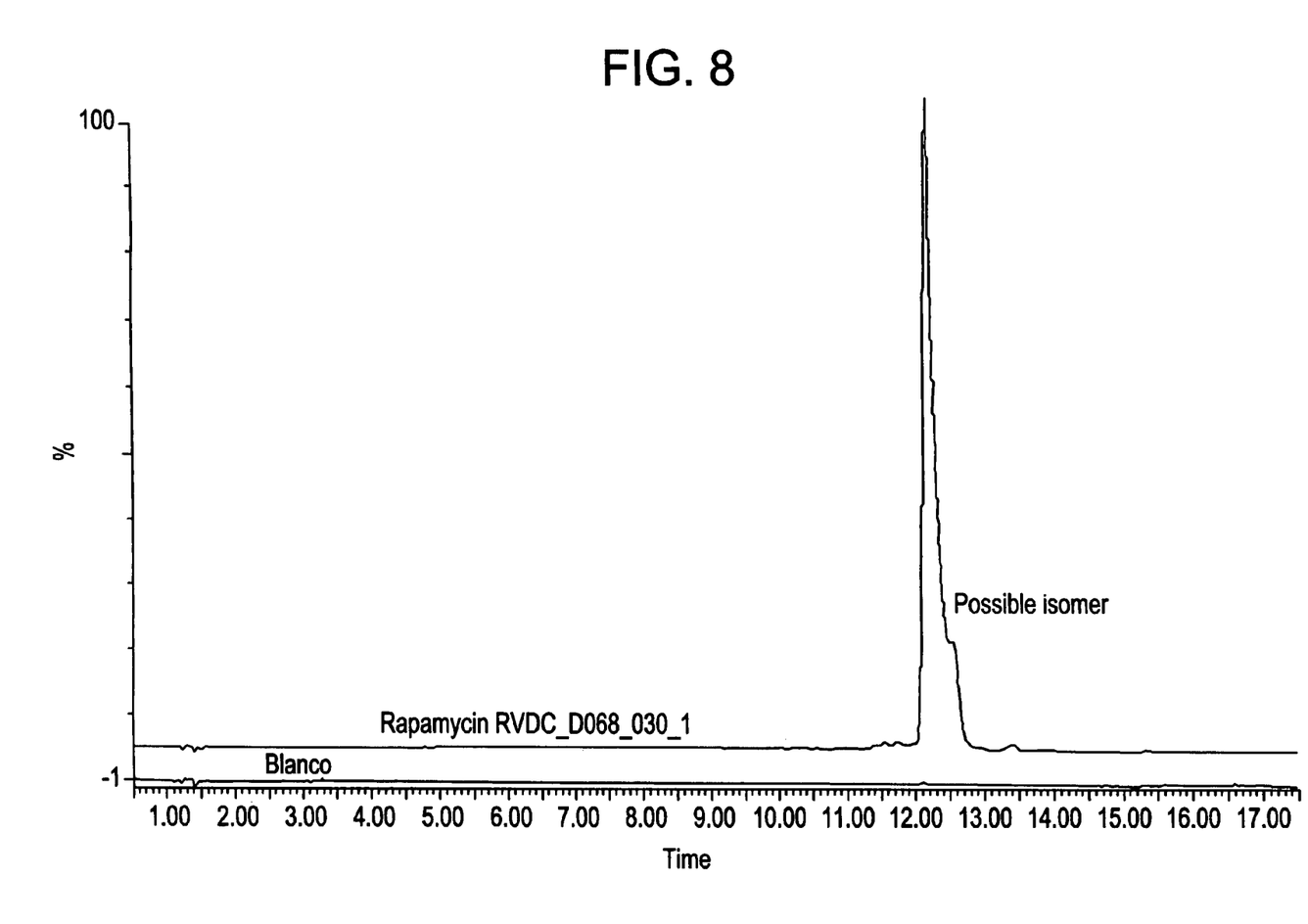
FIG. 8 is a high pressure liquid chromatography-mass spectrometry (LC-MS) trace prepared in accordance with the present invention.

| Temperature program | Step | start temp. in ° C. | Rate in ° C./min. | end temp. in ° C. | hold time in min. | run time in min. |
|---|---|---|---|---|---|---|
| | 1 | 40 | 0 | 40 | 0.5 | 0–0.5 |
| | 2 | 40 | 5 | 165 | 0 | 0.5–25.5 |
| | 3 | 165 | 30 | 220 | 8 | 25.5–35.3 | comment: step 3 is started approximately 2 minutes after elution of chlorobenzene In yet another test the amorphous sirolimus is analyzed using high pressure liquid chromatography-mass spectrometry (LC-MS). Table 5, given below, contains a summary of the test parameters. Essentially, the purpose of this test is to determine if the amorphous sirolimus prepared by the above-described process is degraded in any significant way. FIG. 8 is the LC-MS trace of amorphous sirolimus prepared utilizing the above-described process. LC-MS analysis on solvent free amorphous sirolimus (rapamycin) prepared by the above-described process confirmed the formula by accurate mass. In other words, the sirolimus was not degraded during the process.

TABLE 5

LC-MS

| HPLC System | Parameters | | | |
|---|---|---|---|---|
| Column | Hypersil BDS - 10 cm × 4 mm I.D. and 3 µm particle size comment: | | | |
| Column temperature | 30° C. comment: | | | |
| Flow rate | 1.2 ml/min comment: | | | |
| Injection volume | 5 µl comment: | | | |
| Mobile phase | preparation and composition | | | |
| | A | 0.5% ammonium acetate in water | | |
| | B | acetonitrile | | |
| | comment: | | | |
| | | time in min. | | |
| Gradient | solvent | 0 | 15 | 17 |
| | % A | 90 | 0 | 0 |
| | % B | 10 | 100 | 100 |
| | comment: analytical run time is 15 minutes | | | |

Sirolimus is a rapamycin. Rapamycin is a macrocyclic triene antibiotic produced by Streptomyces hygroscopius as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vascular walls.

Rapamycin reduces vascular hyperplasia by antagonizing smooth muscle proliferation in response to mitogenic signals that are released during vascular injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, rapamycin includes rapamycin and all analogs, derivatives and conjugates that bind to FKBP12, and other immunophilins and possesses the same pharmacological properties as rapamycin, including inhibition of the target of rapamycin (TOR).

Other drugs that may be processed into a substantially solvent free amorphous solid form include 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O-O-(6-Hydroxy)hexyl-rapamycin 40-O-[2-(2-Hydroxy)ethoxy]ethyl-rapamycin 4O-O-[(3S)-2,2-Dimethyldioxolan-3-yl]methyl-rapamycin, 40-O-[(2S)-2,3-Dihydroxyprop-1-yl]-rapamycin, 4O-O-(2-Acetoxy)ethyl-rapamycin 4O-O-(2-Nicotinoyloxy)ethyl-rapamycin, 4O-O-[2-(N-Morpholino)acetoxy]ethyl-rapamycin 4O-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O-O-(2-Aminoethyl)-rapamycin, 4O-O-(2-Acetaminoethyl)-rapamycin 4O-O-(2-Nicotinamidoethyl)-rapamycin, 4O-O-(2-(N-Methyl-imidazo-2'-ylcarbethoxamido)ethyl)-rapamycin, 4O-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method of forming amorphous rapamycin from crystalline rapamycin comprising:

dissolving crystalline rapamycin in 2-propanol to form a solution;

forming an amorphous rapamycin precipitate by adding water to the solution wherein the concentration of rapamycin dissolved in the solution determines a time period within which the precipitate is formed; and minimizing autoxidation of the amorphous rapamycin by reducing exposure thereof to free radicals, residual solvents and autoxidation initiators by using low hydroperoxide solvents, by reducing dissolved oxygen via inert gas blanketing, by increasing the glass transition temperature of the amorphous rapamycin.

* * * * *